(12) United States Patent
Kodama

(10) Patent No.: US 6,587,716 B2
(45) Date of Patent: Jul. 1, 2003

(54) METHOD AND INSTRUMENT FOR ESTIMATING CONDITION OF GROWING OVUM

(75) Inventor: Miyuki Kodama, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 10/001,807

(22) Filed: Dec. 5, 2001

(65) Prior Publication Data

US 2002/0058880 A1 May 16, 2002

(30) Foreign Application Priority Data

Nov. 12, 2000 (JP) ........................................ 2000-375660

(51) Int. Cl.$^7$ ................................................ A61B 5/05
(52) U.S. Cl. ...................................................... 600/547
(58) Field of Search ........................... 435/806; 600/547, 600/551, 587, 591; 128/734, 738

(56) References Cited

U.S. PATENT DOCUMENTS

| | | | |
|---|---|---|---|
| 4,685,471 A | * 8/1987 | Regas et al. ................. | 600/547 |
| 5,086,781 A | * 2/1992 | Bookspan .................... | 600/551 |
| 5,916,173 A | * 6/1999 | Kirsner ........................ | 600/547 |
| 6,434,422 B1 | * 8/2002 | Tomoda et al. ............. | 600/547 |

FOREIGN PATENT DOCUMENTS

JP 09-220209 8/1997

OTHER PUBLICATIONS

Japan Fertilization and Implantation Society Journal 14: (1997), Hoshiai, T. et al., 121–123.

* cited by examiner

Primary Examiner—Max F. Hindenburg
Assistant Examiner—Jonathan Foreman
(74) Attorney, Agent, or Firm—McDermott, Will & Emery

(57) ABSTRACT

An object of the present invention is to know the current hormone balance and condition of the growing ovum of a woman instantaneously by carrying out a simple noninvasive and thereby provide the woman who wishes to become pregnant with sufficient information by informing her of whether she is in a condition in which she is likely to become pregnant at a high success rate. An instrument for estimating the condition of a growing ovum according to the present invention measures a bioelectrical impedance, calculates the index of follicle growth of an examinee from the measured bioelectrical impedance value and at least one parameter pertaining to the physique of the examinee, and compares the calculated index of follicle growth of the examinee with the index of follicle growth as a reference which corresponds to the number of passed days of a menstrual cycle to estimate whether the growing ovum of the examinee is in good condition.

17 Claims, 5 Drawing Sheets

METHOD AND INSTRUMENT FOR ESTIMATING CONDITION OF GROWING OVUM

BACKGROUND OF THE INVENTION

1. Field of the Invention

The present invention relates to a method and an instrument for estimating whether the growing ovarian follicle of a woman who wishes to become pregnant is in good condition.

2. Prior Art

Heretofore, to determine an impregnable period, one who wishes to become pregnant generally practices a method of measuring basal body temperature continuously or a method of detecting hormones in urine by use of test paper after a certain period of time has passed since a menstrual day. This is a method in which the number of fertilizable days is calculated from the fertilizable time of an ovum and the fertilizable time of sperms to determine several days before and after an ovulation day inclusive as the impregnable period. To perform the calculation, the occurrence of ovulation is checked by use of the above method.

Further, as a method for examining the condition of the growing ovum of a woman, a blood collection method or a method of examining the condition of an uterus or oviduct directly has been practiced.

Further, Japan Fertilization and Implantation Society Journal 14: (1997) 121–123 discusses the transition of a body impedance value in external fertilization and ovulation induction. The journal discusses that a growing ovum is in good condition when the body impedance value is higher than a given impedance value.

Although the conventional methods for determining an impregnable period can determine when the impregnable period is, they are not capable of determining a physical condition suitable for impregnation and the condition of a growing ovum.

A conventional method for examining whether one is in a physical condition suitable for impregnation causes pain on the examinee and takes time because it involves the collection of blood and the direct examination of the condition of an uterus or oviduct and therefore puts significant burdens on the examinee physically as well as mentally. In addition, the method requires a certain amount of time to reveal the result of the examination and is not capable of determining whether the examinee is in the physical condition suitable for impregnation easily.

Further, it is also described in the above "Japan Fertilization and Implantation Society Journal 14: (1997) 121–123" that the condition of a growing ovum can be known based on a change in body impedance value. However, since the body impedance varies according to the physique of an individual, it is difficult to know the condition of the growing ovum by simply measuring the bioelectrical impedance.

The present invention has been invented in view of these conventional problems. An object of the present invention is to know the current hormone balance and condition of the growing ovum of a woman instantaneously by carrying out a simple noninvasive measurement and thereby provide the woman who wishes to become pregnant with sufficient information by informing her of whether she is in a condition in which she is likely to become pregnant at a high success rate.

SUMMARY OF THE INVENTION

A method of the present invention for estimating the condition of a growing ovum comprises the steps of measuring a bioelectrical impedance, calculating the index of follicle growth of an examinee from the measured bioelectrical impedance value and at least one parameter pertaining to the physique of the examinee, and comparing the calculated index of follicle growth of the examinee with the index of follicle growth as a reference which corresponds to the number of passed days of a menstrual cycle to estimate whether the growing ovum of the examinee is in good condition.

Further, a method of the present invention for estimating the condition of a growing ovum comprises the steps of measuring a bioelectrical impedance by use of alternating currents of a plurality of frequencies, calculating the index of follicle growth of an examinee from the measured bioelectrical impedance value and at least one parameter pertaining to the physique of the examinee, and comparing the calculated index of follicle growth of the examinee with the index of follicle growth as a reference which corresponds to the number of passed days of a menstrual cycle to estimate whether the growing ovum of the examinee is in good condition.

Further, a method of the present invention for estimating the condition of a growing ovum comprises the steps of measuring a bioelectrical impedance and comparing the measured bioelectrical impedance value with the past bioelectrical impedance value measured in the relative period of an examinee.

Further, in the method of the present invention for estimating the condition of a growing ovum, the index of follicle growth as a reference which corresponds to the number of passed days of a menstrual cycle is modified according to the age of the examinee.

Further, in the method of the present invention for estimating the condition of a growing ovum, the at least one parameter pertaining to the physique of the examinee is a height.

Further, in the method of the present invention for estimating the condition of a growing ovum, the at least one parameter pertaining to the physique of the examinee is a weight.

Further, in the method of the present invention for estimating the condition of a growing ovum, the at least one parameter pertaining to the physique of the examinee is BMI.

An instrument of the present invention for estimating the condition of a growing ovum comprises an input unit, a bioeilectrical impedance measuring unit, an arithmetic unit, a comparing unit, an estimating unit and an informing unit, wherein the input unit inputs at least one parameter pertaining to the physique of an examinee, the bioelectrical impedance measuring unit measures the bioelectrical impedance of the examinee, the arithmetic unit calculates the index of follicle growth of the examinee from the measured bioelectrical impedance and the parameter pertaining to the physique of the examinee, the comparing unit compares the calculated index of follicle growth of the examinee with the index of follicle growth as a reference which corresponds to the number of passed days of a menstrual cycle, the estimating unit estimates the condition of the growing ovum of the examinee based on the result of the comparison, and the informing unit informs the result pertaining to the condition of the growing ovum from the estimating unit.

Further, an instrument of the present invention for estimating the condition of a growing ovum comprises an input unit, a bioelectrical impedance measuring unit, an arithmetic unit, a comparing unit, an estimating unit and an informing unit, wherein the input unit inputs at least one parameter pertaining to the physique of an examinee, the bioelectrical impedance measuring unit measures the bioelectrical impedance of the examinee by use of alternating currents of a plurality of frequencies, the arithmetic unit calculates the index of follicle growth of the examinee from the measured bioelectrical impedance and the parameter pertaining to the physique of the examinee, the comparing unit compares the calculated index of follicle growth of the examinee with the index of follicle growth as a reference which corresponds to the number of passed days of a menstrual cycle, the estimating unit estimates the condition of the growing ovum of the examinee based on the result of the comparison, and the informing unit informs the result pertaining to the condition of the growing ovum from the estimating unit.

Further, an instrument of the present invention for estimating the condition of a growing ovum comprises a bioelectrical impedance measuring unit, a memory, a comparing unit, an estimating unit and an informing unit, wherein the bioelectrical impedance measuring unit measures the bioelectrical impedance of an examinee, the comparing unit compares the current bioelectrical impedance with the bioelectrical impedance in the past relative period which is stored in the memory, the estimating unit estimates the condition of the growing ovum of the examinee based on the result of the comparison, and the informing unit informs the result pertaining to the condition of the growing ovum from the estimating unit.

Further, in the instrument of the present invention for estimating the condition of a growing ovum, the index of follicle growth as a reference is modified according to the examinee's age input through the input means.

Further, the instrument of the present invention for estimating the condition of a growing ovum further comprises a memory, wherein the memory stores the measured bioelectrical impedance and the comparing unit compares the measured bioelectrical impedance with the past bioelectrical impedance in the relative period which is stored in the memory when the estimated condition of the hormone is good.

Further, in the instrument of the present invention for estimating the condition of a growing ovum, the at least one parameter pertaining to the physique of the examinee is a height.

Further, in the instrument of the present invention for estimating the condition of a growing ovum, the at least one parameter pertaining to the physique of the examinee is a weight.

Further, in the instrument of the present invention for estimating the condition of a growing ovum, the at least one parameter pertaining to the physique of the examinee is BMI.

Further, the instrument of the present invention for estimating the condition of a growing ovum further comprises a body weight measuring unit, wherein the body weight measuring unit measures the body weight of the examinee and the measured body weight is used as the parameter pertaining to the physique of the examinee.

Further, in the instrument of the present invention for estimating the condition of a growing ovum, the index of follicle growth is the ratio between extracellular fluid resistance and intracellular fluid resistance.

Figure 1:
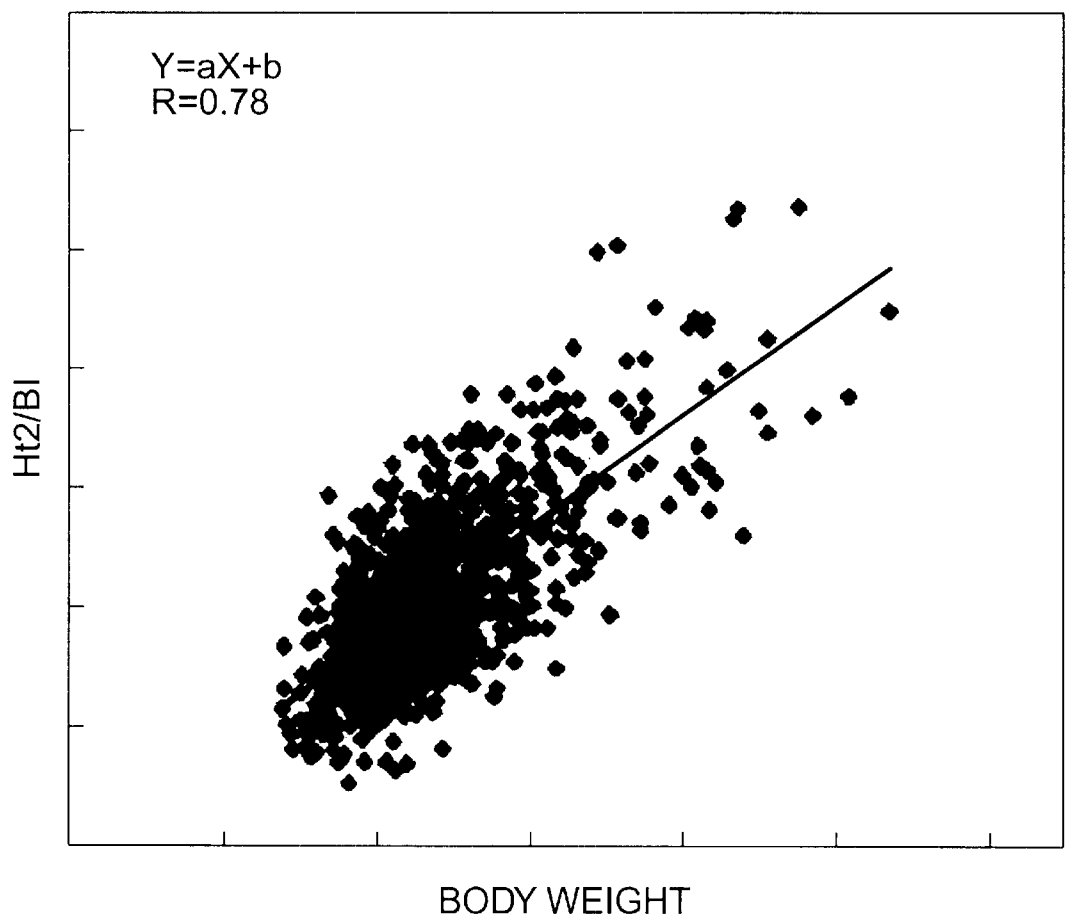
FIG. 1 is a diagram showing the relationship between height$^2$/BI and a body weight.

Reference numeral 1 denotes a physical condition examining instrument; 2 a weight scale; 3A, 3B, 13A and 13B current feeding electrodes; 4A, 4B, 14A and 14B voltage measuring electrodes; 5A and 5B handgrips; 6A and 6B codes; 7A and 7B grip holders; 8 a touch panel; 10 a CPU; 21 a current feeding section; 22 a voltage measuring section; 23 a weight sensor; and 24 a memory.

DETAILED DESCRIPTION OF THE PREFERRED EMBODIMENTS

A bioelectrical impedance (hereinafter referred to as "BI") is proportional to the traveling distance (length of a body part in a living body) of current and inversely proportional to the cross-sectional area (thickness of the body part) of the current. It is said according to the relationship that height$^2$/BI is proportional to a total body water (TBW). Further, the TBW is said to be generally 50 to 60% of a body weight.

FIG. 1 is a diagram showing the relationship between a bioelectrical impedance (hereinafter referred to as "BI") and a body weight. As shown in FIG. 1, although a direct proportional relationship is actually seen between the BI and the body weight, the relationship varies according to such factors as the degree of swelling.

Incidentally, it is said that water and electrolytes are out of balance when an imbalance in hormones is serious enough to adversely affect the growth of an ovum. It is known that estrogens and progesterones in female sex hormones mature the ovum, induce ovulation and maintain an fertilized ovum and both of them are deeply related to a change in the retained water content of a body and a change in electrolytes in the blood.

Meanwhile, when luteinizing hormones (LH) in the female sex hormones are secreted too early, they luteinize a maturing ovarian follicle too early, thereby inhibiting the growth of the ovum. The above progesterones are secreted from the corpus luteum after ovulation, and an increase in the progesterones lowers a BI value since it retains water in a body. That is, the condition of a growing ovum is determined to be poor when the BI value is low.

The present invention uses the above relationship to determine the condition of the growing ovum of an examinee by calculating a value pertaining to the condition of the growing ovum from a BI measured within a given period (high temperature phase or low temperature phase) of a menstrual cycle and the physical information of the examinee such as her height or weight and comparing the value with a reference value.

An embodiment of the present invention will be described with reference to the drawings.

Figure 2:
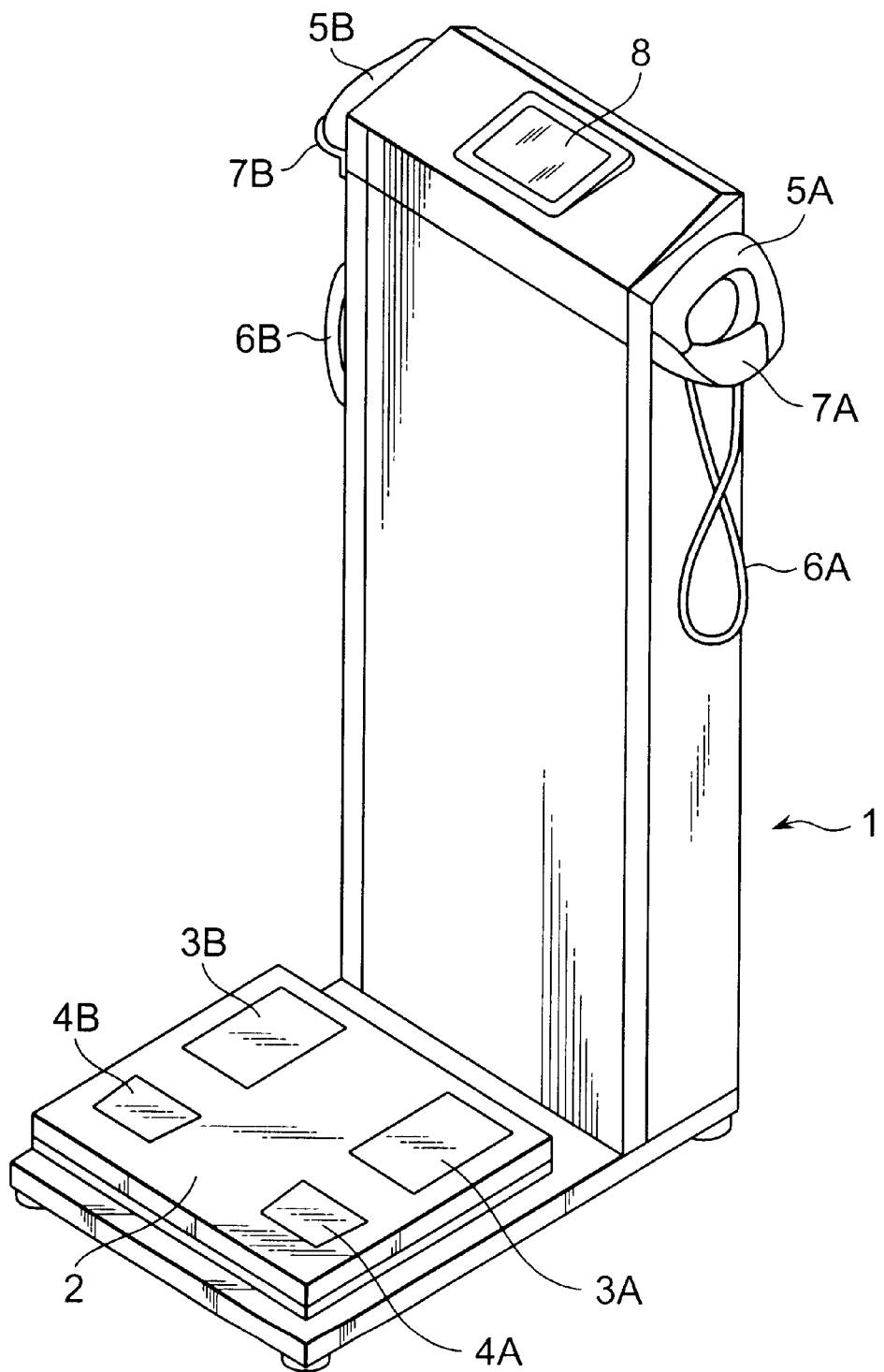
FIG. 2 is a diagram showing the appearance of the instrument of an embodiment of the present invention.

FIG. 2 is a diagram showing the appearance of the examination instrument of the present invention.

The instrument of the present invention for examining a physical condition is an instrument with electrodes for hands and feet which is capable of measuring the bioelectrical impedance of a whole body. The main body of an examination instrument 1 is shaped like a letter L and has a known weight scale 2 as means for measuring a body weight value at its lower portion. The scale 2 has electrodes 3A, 3B, 4A and 4B for feet on its measuring surface. These electrodes are disposed such that they make contact with the bottoms of the feet of an examinee at the time of measurement. The electrodes 3A, 3B, 4A and 4B make contact with the toe of the right foot, the toe of the left foot, the heel of the right foot and the heel of the left foot, respectively. The electrodes 3A and 3B are current feeding electrodes as means for feeding a current to a living body, and the electrodes 4A and 4B are voltage measuring electrodes as means for measuring the impedance of the living body.

To the sides of the upper portion of the main body of the instrument 1, a handgrip 5A for the right hand and a handgrip 5B for the left hand are connected via codes 6A and 6B, respectively, and grip holders 7A and 7B for holding the handgrips 5A and 5B are also provided. These grip holders 7A and 7B are intended for holding the handgrips 5A and 5B at all times other than when the impedance of a living body is measured. Further, the handgrip 5A has a current feeding electrode 13A and a voltage measuring electrode 14A, and the handgrip 5B has a current feeding electrode 13B and a voltage measuring electrode 14B. These electrodes are disposed such that they make contact with the palms of an examinee when she grips the handgrips 5A and 5B.

At the top of the main body of the instrument 1, a display as informing means is provided. The display incorporates an LCD module 8 with a touch panel (hereinafter simply referred to as "touch panel") and has not only the function of displaying the results of measurement, personal setting information and a "standby" status but also a key entry function implemented by the touch panel function. Therefore, the display also serves as input means through which the personal information of an examinee such as a height, gender and age as well as other information can be input at the presses of switches displayed on the touch panel 8 at the initiation of the measurement.

Figure 3:
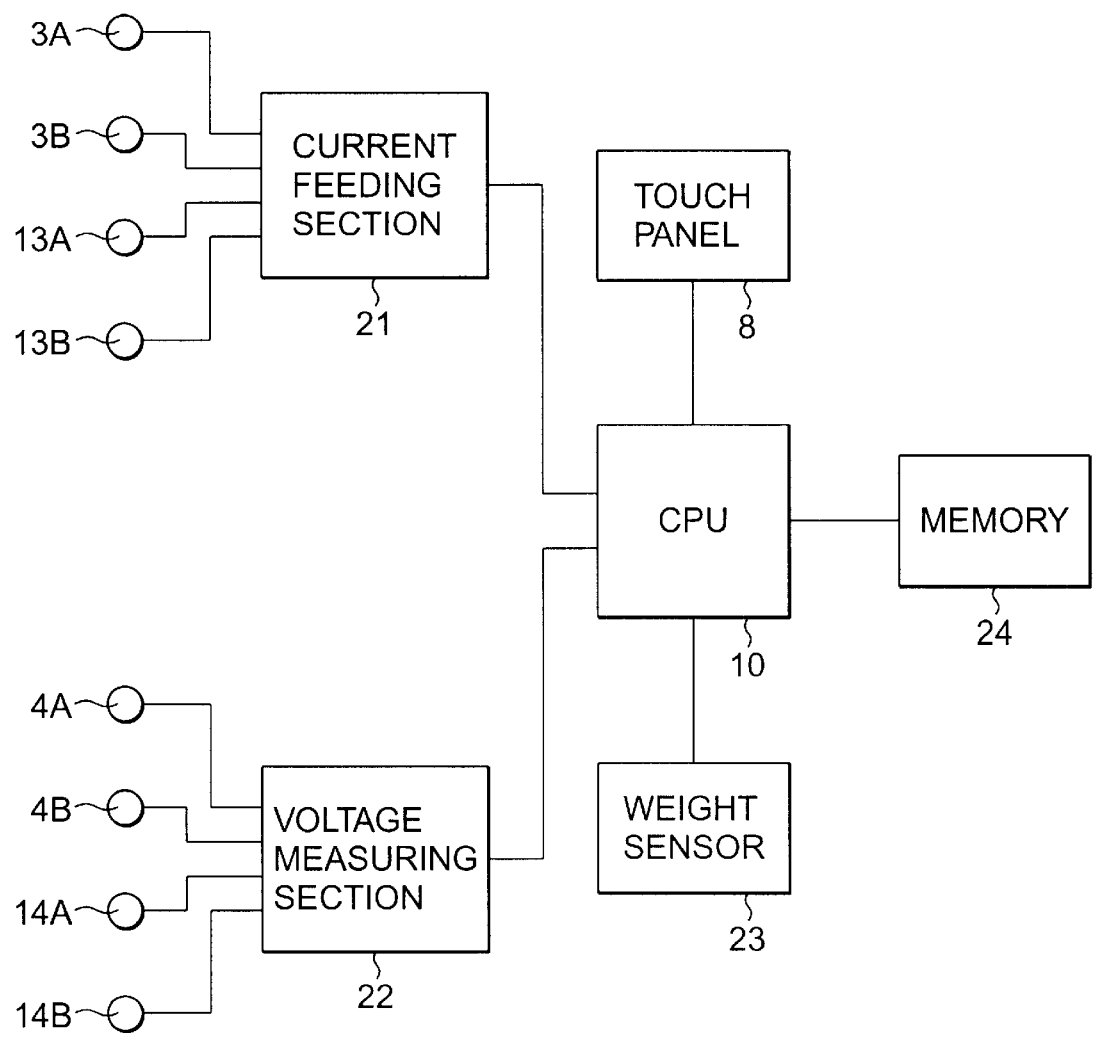
FIG. 3 is a block diagram showing the internal constitution of the instrument of the embodiment of the present invention.

FIG. 3 is a block diagram showing the internal constitution of the physical condition examining instrument shown in FIG. 2. In the present physical condition examining instrument 1, a CPU 10 which performs a variety of computations and exercises a variety of control is connected to a current feeding section 21 which is current feeding means comprising a constant current circuit which generates a constant current used as a measuring current in response to the processing command from the CPU 10, and the output terminals of the current feeding section are connected to the current feeding electrodes 3A, 3B, 13A and 13B.

The voltage measuring electrodes 4A, 4B, 14A and 14B are connected to a voltage measuring section 22 which is voltage measuring means. The voltage measuring section 22 comprises a detector circuit which shapes the amplified waveform of a measured voltage and an A/D converter which converts the analog data of the shaped voltage waveform into the corresponding digital data, and the digital data generated by the A/D converter is input into the CPU 10. Further, the CPU 10 is also connected to the weight sensor 23 of the scale 2 to measure a body weight.

In addition, the CPU 10 is also connected to a memory 24 which is storage means for storing measured bioelectrical impedance value and body weight and the preset personal information of an examinee as well as a reference value used as a criterion for a physical condition and to the touch panel 8.

The CPU 10 serves as arithmetic means for computing the index of follicle growth from the measured bioelectrical impedance value and the stored preset personal information, comparing means for comparing the calculated index of follicle growth with the reference value and estimating means for estimating the condition of the growing ovum of the examinee.

Figure 4:
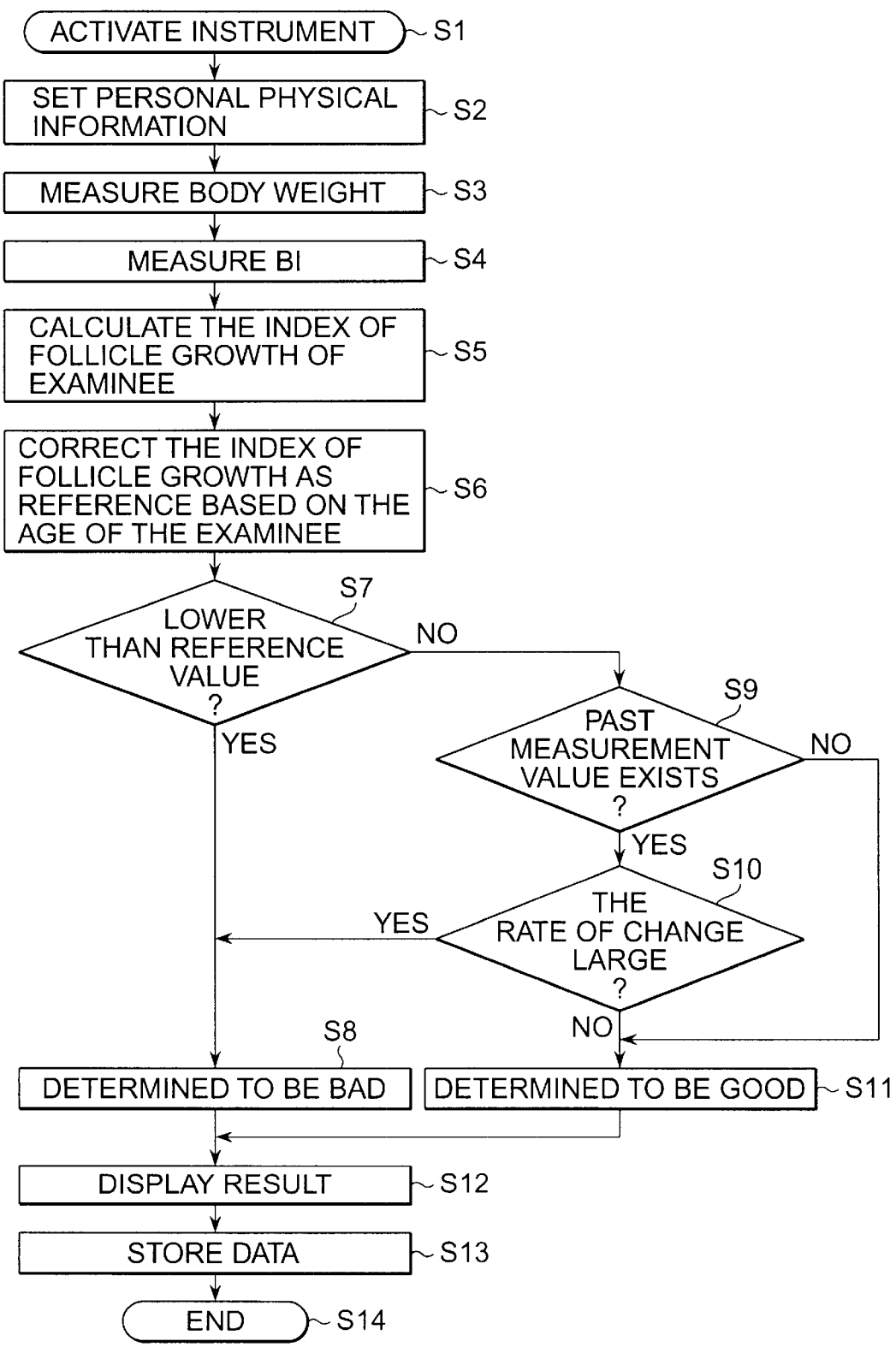
FIG. 4 is a flowchart showing the operational procedures of the first embodiment of the present invention.

Next, the operational procedures of the present embodiment will be described in detail with reference to the flowchart shown in FIG. 4.

The following measurement is intended for examining the physical condition of an examinee in an examination facility such as a hospital. It is desirable to measure the physical condition of the examinee from five to seven days after the beginning of menstruation or within three days after an increase in body temperature caused by ovulation in a menstrual cycle. This is because hormone secretion is generally active during these periods and a change in bioelectrical impedance due to the active hormone secretion can be detected easily.

The instrument is activated when an examinee depresses a measurement starting button on the touch panel 8 which is an input device (STEP S1).

Then, the instrument waits for the examinee to input personal physical information. The examinee inputs an management number and each item of her personal physical information including a height, an age and the condition in a menstrual cycle. The "condition in a menstrual cycle" means a physical condition pertaining to the present menstruation, and the number of days passed from the menstruation and whether the present measurement will be carried out after the menstruation or after ovulation are set (STEP S2).

Then, the examinee stands on bare feet on the scale 2 of the instrument 1 such that the bottoms of her feet make contact with the electrodes of the scale 2. At this point, the examinee stands on the scale 2 such that the toe and heel of the right foot make contact with the current electrode 3A and the voltage electrode 4A and the toe and heel of the left foot make contact with the current electrode 3B and the voltage electrode 4B, respectively. At this point, the measuring device starts measuring the body weight of the examinee upon detection of a load. The measured body weight value is stored in the memory 24 (STEP S3).

Then, a message which urges the examinee to grip the handgrips is displayed on the touch panel 8. The examinee grips the handgrips 5A and 5B with both hands such that the current feeding electrodes 13A and 13B and the voltage measuring electrodes 14A and 14B make contact with her palms.

Then, the CPU 10 starts measuring a bioelectrical impedance. Two current feeding electrodes are selected from the current feeding electrodes connected to the current feeding section 21, and an alternating current is fed between the selected current feeding electrodes. Meanwhile, two electrodes are selected from the voltage measuring electrodes connected to the voltage measuring section 22, and a voltage between the selected voltage measuring electrodes is measured. Such a measurement is repeated with a different combination of current feeding electrodes and a different combination of voltage measuring electrodes to calculate the bioelectrical impedance of the whole body of the examinee. The calculated bioelectrical impedance is stored in the memory 24 (STEP S4).

Then, the index of follicle growth of the examinee is calculated from the measured BI value, measured body weight value and preset personal physical information stored in the memory 24.

The index of follicle growth is calculated by the following methods.

(a) method using a height and a body weight index of follicle growth: $IFG_1 = a \times body\ weight - b \times (height^2/BI) + c$ wherein a, b and c are coefficients.

(b) method using $BMI = body\ weight/height^2$ index of follicle growth: $IFG_2 = BMI/BI$ or $IFG_3 = BI/BMI$ The calculation of the index of follicle growth uses such parameters as a height and a weight to correct a variation in the BI value which depends on an individual physique (STEP S5).

Further, the index of follicle growth as a reference which corresponds to the number of passed days of a menstrual cycle is corrected based on the age of the examinee. The index of follicle growth as a reference is the index of follicle growth $IFG_1$, $IFG_2$ or $IFG_3$ calculated in the above (a) or (b) from the average BI value of normal women who are at the reproductive ages of 30 to 39. The reference value corresponding to the number of passed days of the menstrual cycle is stored in the memory 24 in advance. However, when the examinee is younger than 30 years old, the index of follicle growth corresponding to 120% of the normal reference value is used as a reference, while when the examinee is 40 years old or older, the index of follicle growth corresponding to 80% of the normal reference value is used as a reference. When the examinee is a young woman, the index of follicle growth is compared with a reference value higher than the normal reference value to estimate the condition of a growing ovum, because the younger she is, the more active ovum cell division is and the higher the fertility of the ovum itself is, so that she can still become pregnant even when her hormones are somewhat out of balance, while when the examinee is an old woman, the index of follicle growth is compared with a reference value lower than the normal reference value to estimate the condition of a growing ovum because she has a lower reproductive ability (STEP S6). When the $IFG_3$ is used as the index of follicle growth, the index of follicle growth corresponding to 80% of the normal reference value is used as a reference when the examinee is younger than 30 years old, while the index of follicle growth corresponding to 120% of the normal reference value is used as a reference when the examinee is 40 years old or older.

Then, the measured index of follicle growth is compared with the index of follicle growth as a reference which is stored in the memory 24 and corresponds to the number of passed days of the menstrual cycle (STEP S7). When the measured index of follicle growth is lower than the index of follicle growth as a reference, the condition of hormones, that is, the condition of the growing ovum, is determined to be bad (STEP S8).

In the STEP S7, when the calculated index of follicle growth of the examinee is higher than the index of follicle growth as a reference which corresponds to the number of passed days of the menstrual cycle, it is further determined whether any BI value (relative BI value) in a relative period which has been measured within the last two months is stored in the memory 24 (STEP S9). The relative period is the relationship between a high temperature phase and a low temperature phase in the menstrual cycle. The measurement after menstruation corresponds to the high temperature phase, and the measurement after ovulation corresponds to the low temperature phase. That is, it is determined whether the measured value after the ovulation is stored in the memory 24 when the present measurement is the measurement after the menstruation, while it is determined whether the measured value after the menstruation is stored in the memory 24 when the present measurement is the measurement after the ovulation.

The BI value in the relative period must be the one measured within the last two months because the physical condition of a woman undergoing the menstrual cycle is liable to be changed even by such a mental condition as stress and a comparison with an old BI value lacks accuracy and because only the values measured in the last two cycles should exist in the last two months at the maximum in the case of a normal person. When a plurality of relative BI values exist, the oldest relative BI value is used.

When the relative BI value exists, the rate of change between the current BI value and the relative BI value is calculated. When the rate of change is larger than a given value, it indicates that the body of the examinee is undergoing rapid swelling due to an imbalance in hormones. In this case as well, the condition of the growing ovum is determined to be bad (STEP S10).

When the calculated index of follicle growth of the examinee is lower than the index of follicle growth as a reference which corresponds to the number of passed days of the menstrual cycle and the relative BI value does not exist or the rate of change is small even if the relative BI value exists, it is determined that the growing ovum is in good condition, that is, the examinee is in a physical condition suitable for impregnation (STEP S11). Meanwhile, when the calculated index of follicle growth of the examinee is higher than the index of follicle growth as a reference which corresponds to the number of passed days of the menstrual cycle, it is determined that the growing ovum is not in good condition, that is, the examinee is not in the physical condition suitable for impregnation, and the instrument proceeds to STEP S8.

As described above, the physical condition examining instrument of the present embodiment compares the current index of follicle growth of the examinee with the index of follicle growth of normal women and with the past BI value of the examinee herself. Therefore, the condition of the growing ovum can be examined more accurately.

The result of the examination is displayed on the touch panel 8 (STEP S12). When the condition of the growing ovum is determined to be bad as the result of the examination, the examinee is recommended to undergo such an infertility test as a blood test or Huhner test and advised to adapt to diets which stabilize the condition of hormones and make her daily life as stress-free as possible in order to improve her physical condition.

Thereafter, the current physical condition in the menstrual cycle of the examinee which has been input in STEP S2, the measured BI value and the date of the measurement are stored in the memory space corresponding to the management number of the examinee in the memory 24 (STEP S13) and the measurement ends (STEP S14).

As a second embodiment of the present invention, an instrument for determining a physical condition pertaining to impregnation by measuring a bioelectrical impedance by use of alternating currents of a plurality of frequencies will be described hereinafter.

The appearance and block diagram of the instrument of the second embodiment will be omitted since they are the same as FIGS. 2 and 3. In the above multiple-frequency bioelectrical impedance measurement, the current feeding section 21 of FIG. 3 comprises a frequency control circuit and an alternating current output circuit in order to output alternating currents of a plurality of frequencies. The frequency control circuit outputs a signal of a different frequency based on the measurement parameter from the CPU 10, and the output current of the alternating current output circuit is determined based on the signal.

Figure 5:
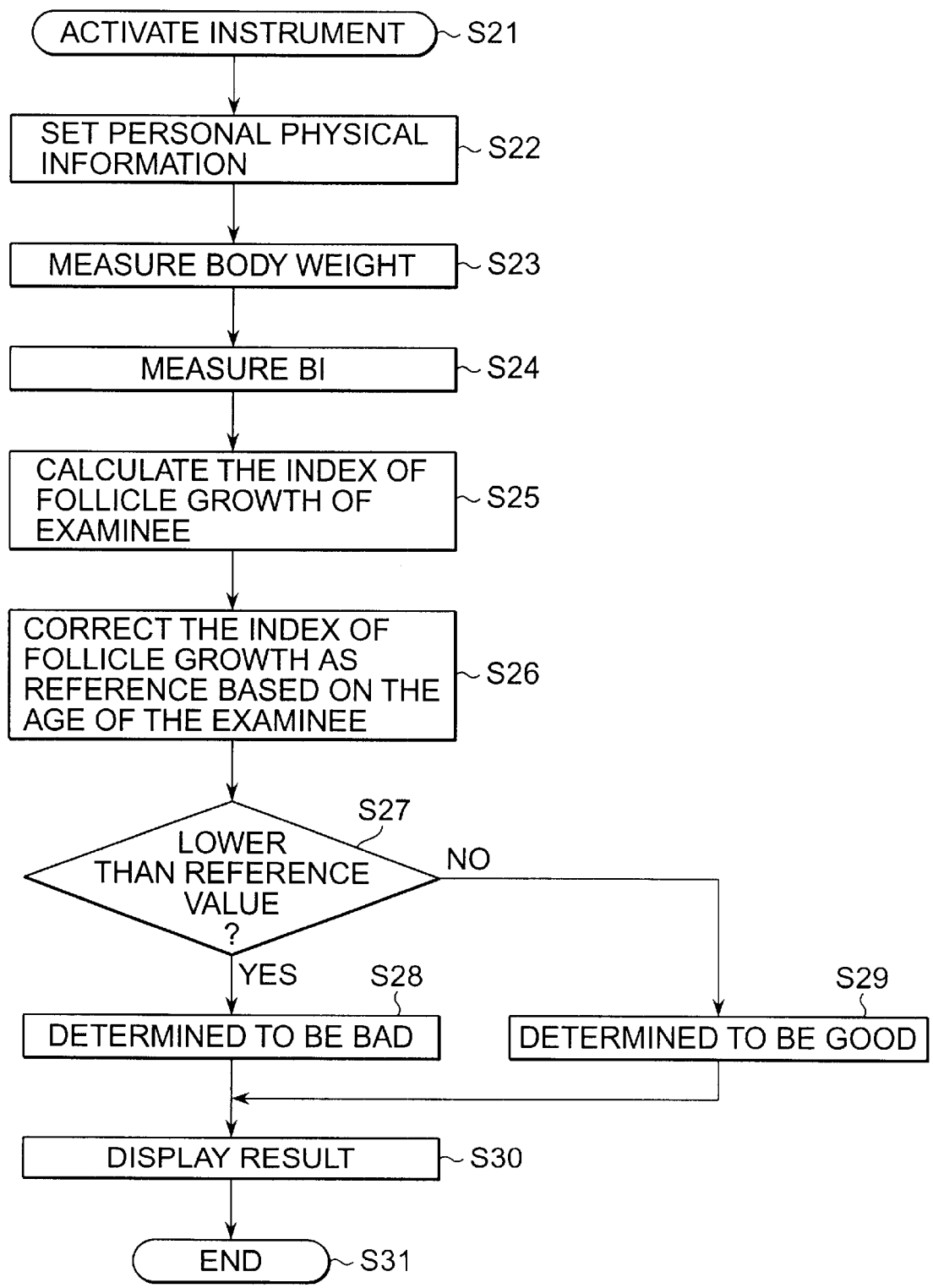
FIG. 5 is a flowchart showing the operational procedures of the second embodiment of the present invention.

Next, the flow of the measurement will be described with reference to the flowchart of FIG. 5. As in the case of the measurement in the first embodiment, the measurement in the second embodiment is also intended for examining the physical condition of an examinee in an examination facility such as a hospital. It is desirable to measure the physical condition of the examinee from five to seven days after the beginning of menstruation or within three days after an increase in body temperature caused by ovulation in a menstrual cycle. This is because hormone secretion is generally active during these periods and a change in bioelectrical impedance due to the active hormone secretion can be detected easily.

The instrument is activated when an examinee depresses a measurement starting button on the touch panel 8 which is an input device (STEP 21).

Then, the instrument waits for the examinee to input personal physical information. The examinee inputs each item of her personal physical information including a height, an age and the condition in a menstrual cycle. The "condition in a menstrual cycle" means the number of days passed from menstruation (STEP S22).

Then, the examinee stands on bare feet on the scale 2 of the instrument 1 such that the bottoms of her feet make contact with the electrodes of the scale 2. At this point, the examinee stands on the scale 2 such that the toe and heel of the right foot make contact with the current electrode 3A and the voltage electrode 4A and the toe and heel of the left foot make contact with the current electrode 3B and the voltage electrode 4B, respectively. At this point, the measuring device starts measuring the body weight of the examinee upon detection of a load. The measured body weight value is stored in the memory 24 (STEP S23).

Then, a message which urges the examinee to grip the handgrips is displayed on the touch panel 8. The examinee grips the handgrips 5A and 5B with both hands such that the current feeding electrodes 13A and 13B and the voltage measuring electrodes 14A and 14B make contact with her palms.

Then, the CPU 10 starts measuring a bioelectrical impedance. Two current feeding electrodes are selected from the current feeding electrodes connected to the current feeding section 21, and an alternating current of a certain frequency is fed between the selected current feeding electrodes. Meanwhile, two electrodes are selected from the voltage measuring electrodes connected to the voltage measuring section 22, and a voltage between the selected voltage measuring electrodes is measured. Such a measurement is repeated with a different combination of current feeding electrodes, a different combination of voltage measuring electrodes and measurement currents of a variety of frequencies to measure a multiple-frequency bioelectrical impedance. The calculated multiple-frequency bioelectrical impedances are in turn stored in the memory 24 (STEP S24).

Then, the index of follicle growth is calculated from the measured BI value, measured body weight value and preset personal physical information stored in the memory 24 and the physical condition of the examinee is examined.

The index of follicle growth is calculated by the following methods.

(c) method using a total body water: TBW and a body weight: w index of follicle growth: $IFG_4 = TBW/w$ is calculated.

(d) method using extracellular fluid resistance: Re and intracellular fluid resistance: Ri index of follicle growth: $IFG_5 = Re/Ri$ is calculated.

The description of a method for measuring the multiple-frequency bioelectrical impedance to calculate the extracellular fluid resistance: Re, intracellular fluid resistance: Ri and whole total body water: TBW of the examinee will be omitted since the method is described in Japanese Patent Application Laid-Open No. 220209-1997 (STEP S25).

Further, the index of follicle growth as a reference which corresponds to the number of passed days of a menstrual cycle is corrected based on the age of the examinee. As in the case of the first embodiment, the index of follicle growth as a reference which corresponds to the number of passed days of the menstrual cycle is the index of follicle growth $IFG_4$ or $IFG_5$ calculated in the above (c) or (d) from the average BI value of normal women who are at the reproductive ages of 30 to 39. The reference value corresponding to the number of passed days of the menstrual cycle is stored in the memory 24 in advance. However, when the examinee is younger than 30 years old, the index of follicle growth corresponding to 120% of the normal reference value is used as a reference, while when the examinee is 40 years old or older, the index of follicle growth corresponding to 80% of the normal reference value is used as a reference. As described in the first embodiment, when the examinee is a young woman, the index of follicle growth is compared with a reference value higher than the normal reference value to estimate the condition of a growing ovum, because the younger she is, the more active ovum cell division is and the higher the fertility of the ovum itself is, so that she can still become pregnant even when her hormones are somewhat out of balance, while when the examinee is an old woman, the index of follicle growth is compared with a reference value lower than the normal reference value to estimate the condition of a growing ovum because she has a lower reproductive ability (STEP S26).

Then, the measured index of follicle growth is compared with the index of follicle growth as a reference which is stored in the memory 24 and corresponds to the number of passed days of the menstrual cycle (STEP S27). When the measured index of follicle growth is lower than the index of follicle growth as a reference which corresponds to the number of passed days of the menstrual cycle, the condition of hormones, that is, the physical condition pertaining to impregnation, is determined to be bad (STEP S28). When the measured index of follicle growth is higher than the index of follicle growth as a reference, the condition of the hormones, that is, the condition of the growing ovum, is determined to be good (STEP S29).

The result of the examination is displayed on the touch panel 8 (STEP S30). When the condition of the growing ovum is determined to be bad as the result of the examination, the examinee is recommended to undergo such an infertility test as a blood test or Huhner test and advised to adapt to diets which stabilize the condition of hormones and make her daily life as stress-free as possible in order to improve her physical condition. Thereafter, the measurement ends (STEP S31).

Although the method for measuring the BI of a whole body has been described as an embodiment of the present invention, the measurement of the BI is no limited to the whole body, and the BI may be measured by use of a portion of the body, e.g., between both feet or between both hands.

Further, although the instruments of the embodiments of the present invention have been described as an instrument capable of measuring not only the BI but also the body weight of the examinee, the body weight as well as other physical information may be input by use of the input means.

In addition, although the instrument of the present invention has been described as an instrument for examining the condition of the growing ovum of one who wishes to become pregnant, the instrument is not limited to such an application and may be used for determining the possibility of hormonal abnormalities such as hyperprolactinemia and corpus luteum deficiency by the measurement of the BI. These symptoms are often impossible to be detected only by a blood test, and the method of the present invention for examining a physical condition by measuring the BI has a better chance of finding a potential patient than an examination based on the measurement of hormones in blood.

The method and instrument of the present invention for examining a physical condition carry out a simple noninvasive measurement to measure the bioelectrical impedance of an examinee, calculate the index of follicle growth from the measured bioelectrical impedance and a parameter pertaining to the physique of the examinee and compares the calculated index of follicle growth with its counterpart of normal women to determine whether a growing ovum is in good condition. Therefore, as compared with conventional examination methods, physical and mental burdens on the examinee are reduced, and the condition of the growing ovum can be known immediately after the measurement. Thus, the method and instrument of the present invention are useful for those who wish to become pregnant.

In addition, the method and instrument of the present invention for examining a physical condition determine the physical condition of the examinee not directly from the measured bioelectrical impedance value of the examinee but by calculating the index of follicle growth from the measured bioelectrical impedance and a parameter pertaining to the physique of the examinee and comparing the calculated value with a reference value. Consequently, there is no variation in the bioelectrical impedance value which depends on the physique of an individual examinee, and it can be determined more accurately whether the growing ovum is in good condition.

What is claimed is:

1. A method for estimating the condition of a growing ovum, comprising the steps of:
    bringing pairs of electrodes into contact with an external skin of an examinee and measuring a bioelectrical impedance between the pairs of the electrodes,
    calculating the index of follicle growth of the examinee from the measured bioelectrical impedance and at least one parameter pertaining to the physique of the examinee, and
    comparing the calculated index of follicle growth of the examinee with the index of follicle growth as a reference which corresponds to the number of passed days of a menstrual cycle to estimate whether the growing ovum of the examinee is in good condition.

2. A method for estimating the condition of a growing ovum, comprising the steps of:
    bringing pairs of electrodes into contact with an external skin of an examinee and measuring a bioelectrical impedance between the pairs of the electrodes by use of alternating currents of a plurality of frequencies,
    calculating the index of follicle growth of the examinee from the measured bioelectrical impedance and at least one parameter pertaining to the physique of the examinee, and
    comparing the calculated index of follicle growth of the examinee with the index of follicle growth as a reference which corresponds to the number of passed days of a menstrual cycle to estimate whether the growing ovum of the examinee is in good condition.

3. A method for estimating the condition of a growing ovum according to claim 1 or 2, wherein the index of follicle growth as a reference which corresponds to the number of passed days of a menstrual cycle is modified according to the age of the examinee.

4. A method for estimating the condition of a growing ovum according to claim 1 or 2, wherein the at least one parameter pertaining to the physique of the examinee is a height.

5. A method for estimating the condition of a growing ovum according to claim 1 or 2, wherein the at least one parameter pertaining to the physique of the examinee is a weight.

6. A method for estimating the condition of a growing ovum according to claim 1 or 2, wherein the at least one parameter pertaining to the physique of the examinee is a BMI.

7. An instrument for estimating the condition of a growing ovum, comprising an input unit, pairs of electrodes, a bioelectrical impedance measuring unit, an arithmetic unit, a comparing unit, an estimating unit, and an informing unit, wherein
    the input unit inputs at least one parameter pertaining to the physique of an examinee,
    the pairs of the electrodes come into contact with an external skin of the examinee,
    the bioelectrical impedance measuring unit measures the bioelectrical impedance of the examinee between the pairs of the electrodes,
    the arithmetic unit calculates the index of follicle growth of the examinee from the measured bioelectrical impedance and the parameter pertaining to the physique of the examinee,
    the comparing unit compares the calculated index of follicle growth of the examinee with the index of follicle growth as a reference which corresponds to the number of passed days of a menstrual cycle,
    the estimating unit estimates the condition of the growing ovum of the examinee based on he result of the comparison, and
    the informing unit informs the result pertaining to the condition of the growing ovum from the estimating unit.

8. An instrument for estimating the condition of a growing ovum, comprising an input unit, pairs of electrodes, a bioelectrical impedance measuring unit, an arithmetic unit, a comparing unit, an estimating unit and an informing unit, wherein
    the input unit inputs at least one parameter pertaining to the physique of an examinee,
    the pairs of the electrodes come into contact with an external skin of the examinee,
    the bioelectrical impedance measuring unit measures the bioelectrical impedance of the examinee between the pairs of the electrodes by use of alternating currents of a plurality of frequencies,
    the arithmetic unit calculates the index of follicle growth of the examinee from the measured bioelectrical impedance and the parameter pertaining to the physique of the examinee, the comparing unit compares the calculated index of follicle growth of the examinee with the index of follicle growth as a reference which corresponds to the number of passed days of a menstrual cycle, the estimating unit estimates the condition of the growing ovum of the examinee based on the result of the comparison, and the informing unit informs the result pertaining to the condition of the growing ovum from the estimating unit.

9. An instrument for estimating the condition of a growing ovum according to claim 7 or 8, wherein the index of follicle growth as a reference is modified according to the examinee's age input through the input means.

10. An instrument for estimating the condition of a growing ovum according to claim 8, which further comprises a memory, wherein the memory stores the measured bioelectrical impedance, and the comparing unit compares the measured bioelectrical impedance with the past bioelectrical impedance in the relative period which is based on the relationship between a high temperature phase and a low temperature phase in a menstrual cycle and which is stored in the memory when the estimated condition of the growing ovum is good.

11. An instrument for estimating the condition of a growing ovum according to any one of claim 7, 8 or 10, wherein the at least one parameter pertaining to the physique of the examinee is a height.

12. An instrument for estimating the condition of a growing ovum according to any one of claim 7, 8 or 10, wherein the at least one parameter pertaining to the physique of the examinee is a weight.

13. An instrument for estimating the condition of a growing ovum according to any one of claim 7, 8 or 10, wherein the at least one parameter pertaining to the physique of the examinee is a BMI.

14. An instrument for estimating the condition of a growing ovum according to any one of claims 7, 8 or 10, the instrument further comprising a body weight measuring unit, wherein the body weight measuring unit measures the body weight of the examinee and the measured body weight is the parameter pertaining to the physique of the examinee.

15. An instrument for estimating the condition of a growing ovum according to claim 8, wherein the index of follicle growth is the ratio between extracellular fluid resistance and intracellular fluid resistance.

16. A method for estimating the condition of a growing ovum, comprising the steps of:

bringing pairs of electrodes into contact with an external skin of an examinee and measuring a bioelectrical impedance between the pairs of the electrodes, and comparing the currently measured bioelectrical impedance with a previously measured bioelectrical impedance;

wherein the previously measured bioelectrical impedance is associated with a high temperature phase of a menstrual cycle of the examinee when the currently measured bioelectrical impedance is associated with a low temperature phase of the menstrual cycle of the examinee; and wherein the previously measured bioelectrical impedance is associated with the low temperature phase of the menstrual cycle of the examinee when the currently measured bioelectrical impedance is associated with the high temperature phase of the menstrual cycle of the examinee.

17. An instrument for estimating the condition of a growing ovum, comprising pairs of electrodes, a bioelectrical impedance measuring unit, a memory, a comparing unit, an estimating unit and an informing unit, wherein the pairs of the electrodes come into contact with an external skin of an examinee, the bioelectrical impedance measuring unit measures the bioelectrical impedance of the examinee between the pairs of the electrodes, the comparing unit compares the currently measured bioelectrical impedance with a past bioelectrical impedance stored in the memory, wherein the past bioelectrical impedance is associated with a high temperature phase of a menstrual cycle of the examinee when the currently measured bioelectrical impedance is associated with a low temperature phase of the menstrual cycle of the examinee, and wherein the past bioelectrical impedance is associated with the low temperature phase of the menstrual cycle of the examinee when the currently measured bioelectrical impedance is associated with the high temperature phase of the menstrual cycle of the examinee, the estimating unit estimates the condition of the growing ovum of the examinee based on the result of the comparison, and the informing unit informs the result pertaining to the condition of the growing ovum from the estimating unit.

\* \* \* \* \*

UNITED STATES PATENT AND TRADEMARK OFFICE
CERTIFICATE OF CORRECTION

PATENT NO. : 6,587,716 B2
DATED : July 1, 2003
INVENTOR(S) : Miyuki Kodama

It is certified that error appears in the above-identified patent and that said Letters Patent is hereby corrected as shown below:

<u>Title page,</u>
Item [30], Foreign Application Priority Data, change the priority date from "Nov. 12, 2000" to -- December 11, 2000 --.

Signed and Sealed this

Fourth Day of November, 2003

JAMES E. ROGAN
*Director of the United States Patent and Trademark Office*